United States Patent [19]

Fogel et al.

[11] Patent Number: 5,116,604

[45] Date of Patent: May 26, 1992

[54] SUNSCREEN COMPOSITIONS CONTAINING NOVEL NEOPENTANOATE ESTERS

[75] Inventors: Arnold W. Fogel, Upper Saddle River; Albert Zofchak, Matawan Township, Monmouth County, both of N.J.

[73] Assignees: Bernel Chemical Co., Englewood; Alzo, Inc., Matawan, both of N.J.

[21] Appl. No.: 765,811

[22] Filed: Sep. 26, 1991

Related U.S. Application Data

[63] Continuation-in-part of Ser. No. 645,334, Jan. 16, 1991, abandoned, which is a continuation-in-part of Ser. No. 335,439, Mar. 20, 1989, abandoned.

[51] Int. Cl.$^5$ .................. A61K 72/42; A61K 7/44; A61K 7/48
[52] U.S. Cl. ........................... 424/59; 424/60; 514/873
[58] Field of Search ..................... 424/59, 60

[56] References Cited

U.S. PATENT DOCUMENTS

| | | | |
|---|---|---|---|
| 4,005,210 | 1/1977 | Gubernick | 514/873 |
| 4,663,155 | 5/1987 | Murray et al. | 514/873 |
| 4,699,781 | 10/1987 | Goupil | 514/873 |
| 4,724,240 | 2/1988 | Arbutyn | 424/60 |

OTHER PUBLICATIONS

Technical Bulletin, Feb. 1989, Suntan Lotion SPF18
AMA Laboratories, Summary Sheet, Feb. 1, 1989, Cantor.
AMA Laboratories Bernel Chem. Co., Table 1 Feb. 1, 1989.
Technical Bulletin, Jan. 1989, Suntan Cream, SPF34.
AMA Laboratories, Summary Sheet, Dec. 12, 1988, Cantor.
AMA Laboratories, Summary Sheet, Nov. 1988, Bernel Chemical Co., Inc.
Technical Bulletin, Jan. 1989, Suntan Cream SPF24.
Technical Bulletin, Feb. 1989, Suntan Cream SPF34/28.
AMA Laboratories Summary Sheet, Dec. 22, 1988, Cantor.
AMA Laboratories, Table 1, Nov. 1988, Bernel Chemical Co. Inc.
Exxon Chemical Exxal 20-Iso Arachidylalcohol Data Sheet, Jun. 16, 1988, pp. 1 to 7.
Technical Bulletin & Summary Sheet, Feb. 1989, SPF34/28, pp. 1 and 2.
Table I, AMALAB, Bernel Chemical, Feb. 1989, p. 1.
Product Identification, Exxal 20-Isoarachidyl Alcohol Jun. 16, 1988 pp. 1 to 4.

*Primary Examiner*—Dale R. Ore
*Attorney, Agent, or Firm*—Anthony D. Cipollone

[57] ABSTRACT

This invention is concerned with the use of neopentanoate esters as novel cosmetic emollients for sunscreen products.

The use of isoarachidyl neopentanoate in sunscreen formulations offer new and unexpected results over the use of similar esters previously disclosed.

The isoarachidyl neopentanoate has a minimal odor, good stability, water white color, higher sun protection factor values, good emolliency, good crystal solibilization, very low freeze point. It forms the emollient basis for a new way to make very high sun protection factor products.

1 Claim, No Drawings

SUNSCREEN COMPOSITIONS CONTAINING NOVEL NEOPENTANOATE ESTERS

The instant application Ser. No. 07/765,811, filed Sep. 26, 1991 as a continuation-in-part of Ser. No. 07/645,334, filed Jan. 16, 1991, which is a continuation-in-part of application Ser. No. 07/335,439, filed Mar. 20, 1989, both now abandoned.

BACKGROUND OF THE INVENTION

1. Field of the Invention

This invention relates to the unique effects and characteristics when novel neopentanoate esters are used in varying concentrations as emollients in conjunction with the active ingredient in sunscreen formulations. The use of the preferred embodiment of this invention, isoarachidyl neopentanoate, offers new and unexpected results from similar esters previously used.

2. Description of Prior Art

U.S. Pat. No. 4,005,210 discloses an emollient for use on the skin which contains isodecyl neopentanoate.

U.S. Pat. No. 4,724,240 discloses the use of carboxylic acid esters as emollients in various types of preparations which include cosmetic and sunscreen applications. It is said that esters which are useful for use as emollients in compositions of this type include esters made from $C_1$-$C_{30}$ alcohols and $C_1$-$C_{30}$ carboxylic acids. Arachidyl proprionate is mentioned as an example of an ester which can be used in the composition of this patent.

U.S. Pat. No. 4,724,240 discloses the use of a broad range of esters (esters made from $C_1$-$C_{30}$ carboxylic acids).

U.S. Pat. No. 4,724,240 specifies the use of arachididyl proprionate for use as an emollient and U.S. Pat. No. 4,005,210 discloses the use of isodecyl neopentanoate as an emollient.

There have been other uses of fatty acid esters as emollients in cosmetic and sunscreen formulations.

OBJECTS AND SUMMARY OF INVENTION

It is the object of this invention to provide novel neopentanoate esters as emollients having unique properties making these esters uniquely suitable in sunscreen formulations.

It is the further object of this invention to provide varying percentages of these unique neopentanoate esters as emollients in sunscreen formulations.

It is believed that the uniqueness of these emollients is due to the reaction of neopentanoic acid and the specific alcohols used [Exxals by Exxon].

These novel neopentanoates exhibit properties unlike other similar esters currently used as emollients. It is these properties, e.g:

(1) Unusual low odor
(2) Good stability at 50° C. for over 3 months
(3) Water white color
(4) Higher SPF values
(5) Good emolliency (light with low residuals)
(6) Good crystal solubilizers
(7) Very low freeze points
(8) Non hydrolyzable in acid pH emulsions
(9) Negative comedogenicity These unique unexpected properties are the focal point of the present invention. The sunscreen products formulated with the instant invention have an unexpected high SPF value.

The preferred embodiment of this invention is Isoarachidyl Neopentanoate formed by reaction of a $C_{20}$ alcohol with neopentanoic acid having the following structure:

$$\underset{CH_3}{\overset{CH_3}{\diagdown}}C_{17}H_{35}CH_2-O-\overset{O}{\overset{\|}{C}}-\underset{CH_3}{\overset{CH_3}{\overset{|}{C}}}-CH_3$$

DETAILED DESCRIPTION OF THE INVENTION

The use of esters as emollients in cosmetic and sunscreen formulations are well known. They are found by the reaction of an organic acid and an alcohol.

$$R_1OH + HO-\overset{O}{\overset{\|}{C}}-R_2 \longrightarrow R_1-O-\overset{O}{\overset{\|}{C}}-R_2$$

where $R_1$ may be:

$$\underset{CH_3}{\overset{CH_3}{\diagdown}}CH-C_{13}H_{26}- \quad \text{isocetyl}$$

$$\underset{CH_3}{\overset{CH_3}{\diagdown}}CH-C_{15}H_{30}- \quad \text{isostearyl}$$

$$\underset{CH_3}{\overset{CH_3}{\diagdown}}CH-C_{17}H_{34}- \quad \text{isoarachidyl}$$

$$\underset{CH_3}{\overset{CH_3}{\diagdown}}CH-C_{23}H_{46}-; \quad \text{isocerotyl}$$

and $R_2$ is $$CH_3-\underset{CH_3}{\overset{CH_3}{\overset{|}{\underset{|}{C}}}}-$$

In the instant invention, the preferred embodiment is formed as follows:

$$\underset{CH_3}{\overset{CH_3}{\diagdown}}CH-C_{17}H_{34}-CH_2OH + HO-\overset{O}{\overset{\|}{C}}-\underset{CH_3}{\overset{CH_3}{\overset{|}{C}}}-CH_3$$

Isoarachidyl Alcohol    Neopentanoic Acid $$\underset{CH_3}{\overset{CH_3}{\diagdown}}C_{17}H_{34}CH_2-O-\overset{O}{\overset{\|}{C}}-\underset{CH_3}{\overset{CH_3}{\overset{|}{C}}}-CH_3$$

Isoarachidyl Neopentanoate

The use of isoarachidyl neopentanoate, the preferred embodiment of the invention, results in products with low odor, good stability and higher S P F values. The isoarachidyl neopentanoate is a clear, water white liquid, has good emolliency and is a good crystal solubilizer when comprising 5%-20% by weight of the sunscreen formulation. It is an extraordinary, silky, unusual emollient which exhibits greater "slip" and significantly enhances the Sun Screen Protective Factor ("S P F"), the isoarachidyl neopentanoate is a low freezing liquid, non-comedogenic, stable and safe.

The isoarachidyl neopentanoate in formulations remains odorless after a minimum of three months storage at 50° C. The fact that it is water white, stable and odorless are unique and novel characteristics of this invention.

These unique properties make the isoarchidyl neopentonoate the preferred emollient in sunscreen formulations.

The $C_{16}$, $C_{18}$ and $C_{26}$ neopentanoates which have also been made using specific alcohols [Exxals by Exxon] for use as sunscreen emollients also exhibit significantly enhanced properties over the present art. However, superior results in sunscreen formulations are obtained when using the preferred embodiment of the invention, isoarachidyl neopentanoate, as the emollient moiety.

Following on the next page are the description and test results of the preferred embodiment of the invention using 10% Elefac, the instant invention in sunscreen formulation F-4-6-2, F-4-8-1, F-4-10-1 and F-4-14,

EXAMPLES

The Formulations

Formula F-4-6-2—Uses 7.5% Parsol MCX and 2% Oxybenzone. We normally would expect an SPF of 18 (on 20 people). We wanted to score the highest SPF possible while keeping the Oxybenzone at a maximum 2% level, with Parsol MCX as the only other U.V. absorber.

Formula F-4-8-1—We were going for maximum SPF with 3 screens, i.e.: Parsol MCX at 7.5% oxybenzone at 6.0% and Octyl Salicylate at 5%. With Bernel Ester DOM in this emulsion, we scored an SPF of 27 (on 20 people), whereas, using 10% Elefac I-205 to replace the "DOM" we scored and SSPF of 34 (on 20 people).

Formula F-4-10-1—We wanted a PABA and PABA Ester free, as well as a Benzophenone free emulsion to give an SPF 15 or above. We scored an SPF of 24 (on 7 people) when we only expected an approximate, SPF of 16-18. Used alone, 7.5% "MCX" yields an SPF of 8 (app.) and 7.5% Hydro, (used alone) also yields an SPF of 8 (app.). When used together, with 10% elefac I-205 added, we scored an SPF of 24.

Formula F-4-14-1—We added 5% Octyl Salicylate and 0.3%, Sodium Metabisulfite to formula F-4-10-1 expecting an SPF of 30 (app.). We scored 35/28 (on 20 people) and again PABA free and Oxybenzone free.

All formulations are "PABA and PABA Ester" free. All score an SPF 15 and above. Some are "Benzophenone" free also.

The Exxal 20 alcohol is the specific alcohol used in manufacturing the neopentanoate emollient used in all the foregoing formulations.

What is claimed is:

1. A sunscreen composition which comprises stearic acid, cetyl alcohol, diethanolamine cetyl phosphate, 100 centistokes silicone fluid, octyl p-methoxy cinnamate, octyl salicylate, deionized water, glycerine, magnesium aluminum silicate, xanthan gum, triethanolamine diethanolamine p-methoxy cinnamate, a preservative, and from 5 to 20% by weight of the composition neopentanoate emollient having the chemical structure as follows:

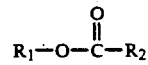

where $R_1$ is a $C_{20}$ alcohol moiety of the neopentanoate ester having the chemical structure:

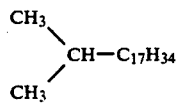

$R_2$ is the acid moiety of the neopentanote having the chemical structure:

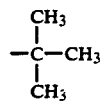

which emollient increases the sunscreen protection factor of the composition, stability and pleasant odorific properties due to the emollient's unique stability.

* * * * *